United States Patent
Gil et al.

(10) Patent No.: US 10,091,986 B2
(45) Date of Patent: Oct. 9, 2018

(54) ORGAN PERFUSION DEVICE AND METHOD

(71) Applicant: XOR-LABS TORONTO INC., Toronto (CA)

(72) Inventors: Lahav Gil, Toronto (CA); Siew Hong Tan, Toronto (CA); Martin Leandro Par, Toronto (CA); Philipp Stücklin, Toronto (CA); Shafique Keshavjee, Toronto (CA); Mingyao Liu, Toronto (CA); Marcelo Cypel, Toronto (CA); David Christopher Lynch, Toronto (CA); Thomas Kenneth Waddell, Toronto (CA); Geoffrey Samuel Frost, Toronto (CA); Grzegorz Piotr Burdyszek, Toronto (CA)

(73) Assignee: XOR-LABS TORONTO INC., Toronto (CA)

( * ) Notice: Subject to any disclaimer, the term of this patent is extended or adjusted under 35 U.S.C. 154(b) by 0 days.

(21) Appl. No.: 15/482,015

(22) Filed: Apr. 7, 2017

(65) Prior Publication Data

US 2017/0318803 A1    Nov. 9, 2017

Related U.S. Application Data

(60) Provisional application No. 62/333,467, filed on May 9, 2016.

(51) Int. Cl.
*C12M 1/00*    (2006.01)
*A01N 1/00*    (2006.01)
*A01N 1/02*    (2006.01)

(52) U.S. Cl.
CPC .................................. *A01N 1/0247* (2013.01)

(58) Field of Classification Search
CPC ...... C12M 21/08; C12M 23/48; C12M 23/44; A01N 1/0236; A01N 1/0247
See application file for complete search history.

(56) References Cited

U.S. PATENT DOCUMENTS

| | | |
|---|---|---|
| 5,494,822 A | 2/1996 | Sadri |
| 5,599,659 A | 2/1997 | Brasile et al. |

(Continued)

FOREIGN PATENT DOCUMENTS

| | | |
|---|---|---|
| CA | 2255657 C | 11/1997 |
| CA | 2304598 C | 4/1999 |

(Continued)

OTHER PUBLICATIONS

Extended European Search Report (EESR) dated Oct. 13, 2017, by EPO, re European Patent Application No. 17170084.2.

*Primary Examiner* — Nathan A Bowers
(74) *Attorney, Agent, or Firm* — Perry + Currier

(57) ABSTRACT

An organ perfusion device includes an inlet for connection to the organ, and an outlet for connection to the organ. The device also includes a perfusion circuit including: a reservoir configured to hold a perfusion fluid; a waste receptacle, and a plurality of fluid conduits. The fluid conduits define: a delivery fluid path connecting the reservoir with the inlet; a return fluid path, independent of the delivery fluid path, connecting the reservoir with the outlet; and a waste fluid path connecting the reservoir with the waste receptacle. The device also includes a first flow control device configured to selectively prevent or allow fluid flow from the reservoir to the organ via the delivery fluid path; and a second flow control device configured to selectively prevent or allow fluid flow from the reservoir to the waste receptacle via the waste fluid path.

22 Claims, 14 Drawing Sheets

(56) References Cited

U.S. PATENT DOCUMENTS

| | | |
|---|---|---|
| 5,643,712 A | 7/1997 | Brasile |
| 5,699,793 A | 12/1997 | Brasile |
| 5,843,024 A | 12/1998 | Brasile |
| 5,856,081 A | 1/1999 | Fahy |
| 6,024,698 A | 2/2000 | Brasile |
| 6,046,046 A | 4/2000 | Hassanein |
| 6,100,082 A | 8/2000 | Hassanein |
| 6,375,613 B1 | 4/2002 | Brasile |
| 6,642,045 B1 | 11/2003 | Brasile |
| 6,794,124 B2 | 9/2004 | Steen |
| 6,953,655 B1 | 10/2005 | Hassanein et al. |
| 7,131,045 B2 | 10/2006 | Guettaf |
| 7,176,015 B2 * | 2/2007 | Alford ............... A01N 1/02 435/284.1 |
| 7,226,427 B2 | 6/2007 | Steen |
| 7,255,983 B2 | 8/2007 | Steen |
| 7,270,833 B2 | 9/2007 | Steen |
| 7,410,474 B1 | 8/2008 | Friend et al. |
| 7,504,201 B2 | 3/2009 | Taylor et al. |
| 7,572,622 B2 | 8/2009 | Hassanein et al. |
| 7,651,835 B2 | 1/2010 | Hassanein et al. |
| 7,678,563 B2 | 3/2010 | Wright et al. |
| 7,749,693 B2 | 7/2010 | Brassil et al. |
| 7,824,848 B2 | 11/2010 | Owen et al. |
| 7,985,536 B2 | 7/2011 | Brasile |
| 8,012,677 B2 | 9/2011 | Steen |
| 8,585,380 B2 | 11/2013 | Hassanein et al. |
| 9,247,728 B2 | 2/2016 | Fishman et al. |
| 2004/0224298 A1 * | 11/2004 | Brassil ............... A01N 1/02 435/1.1 |
| 2005/0147958 A1 | 7/2005 | Hassanein et al. |
| 2005/0221269 A1 | 10/2005 | Taylor et al. |
| 2006/0141623 A1 * | 6/2006 | Smith ............... C12M 21/08 435/383 |
| 2006/0148062 A1 | 7/2006 | Hassanein et al. |
| 2006/0154357 A1 | 7/2006 | Hassanein et al. |
| 2006/0160204 A1 | 7/2006 | Hassanein et al. |
| 2006/0292544 A1 | 12/2006 | Hassanein et al. |
| 2007/0275364 A1 | 11/2007 | Hassanein et al. |
| 2008/0017194 A1 | 1/2008 | Hassanein et al. |
| 2008/0234768 A1 | 9/2008 | Hassanein et al. |
| 2008/0286747 A1 | 11/2008 | Curtis et al. |
| 2009/0197240 A1 | 8/2009 | Fishman et al. |
| 2010/0028850 A1 | 2/2010 | Brassil et al. |
| 2010/0316705 A1 | 12/2010 | Brasile et al. |
| 2010/0326443 A1 | 12/2010 | Steen et al. |
| 2011/0003275 A1 | 1/2011 | Steen et al. |
| 2011/0033916 A1 * | 2/2011 | Hutzenlaub ............... A01N 1/02 435/284.1 |
| 2011/0053256 A1 | 3/2011 | Owen et al. |
| 2011/0065169 A1 | 3/2011 | Steen et al. |
| 2011/0076666 A1 | 3/2011 | Brassil et al. |
| 2011/0136096 A1 | 6/2011 | Hassanein et al. |
| 2011/0144006 A1 | 6/2011 | Steen et al. |
| 2011/0183310 A1 | 7/2011 | Kravitz et al. |
| 2011/0269112 A1 | 11/2011 | Steen et al. |
| 2011/0270215 A1 | 11/2011 | Steen et al. |
| 2011/0281794 A1 | 11/2011 | Steen et al. |
| 2011/0305798 A1 | 12/2011 | Steen et al. |
| 2015/0264918 A1 * | 9/2015 | Hassanein ............... A01N 1/02 435/1.2 |

FOREIGN PATENT DOCUMENTS

| | | |
|---|---|---|
| CA | 2369159 C | 10/2000 |
| CA | 2376607 A1 | 10/2000 |
| CA | 2521324 A1 | 10/2004 |
| CA | 2554872 A1 | 5/2005 |
| CA | 2584066 A1 | 4/2006 |
| CA | 2620328 A1 | 3/2007 |
| CA | 2649703 A1 | 11/2007 |
| CA | 2679827 A1 | 9/2008 |
| CA | 2685302 A1 | 12/2008 |
| CA | 2713443 A1 | 8/2009 |
| DE | 4141129 A1 | 6/1993 |
| WO | WO-02089571 A1 | 11/2002 |
| WO | WO-2015138263 A1 | 9/2015 |

* cited by examiner

ORGAN PERFUSION DEVICE AND METHOD

CROSS-REFERENCE TO RELATED APPLICATION

This application claims priority from U.S. provisional application No. 62/333,467, filed May 9, 2016, the contents of which is incorporated herein by reference.

FIELD

The specification relates generally to donor organ management, and specifically to an organ perfusion device and method.

BACKGROUND

Donor organs such as lungs are highly perishable, and must therefore be transplanted into a recipient as soon as possible following removal from a donor. Traditionally, donor organs were simply stored in ice until implantation into the recipient. More recently, systems for perfusing organs before implantation have been developed to extend the available window of time in which the organs remain viable. However, such systems are often complex and expensive; the expense of such systems is accentuated by their heavy reliance on disposable, single-use components. Such systems can also be difficult to transport.

SUMMARY

According to an aspect of the specification, an organ perfusion device is provided, including: (i) an inlet for connection to the organ, and an outlet for connection to the organ; (ii) a perfusion circuit including: a reservoir configured to hold a perfusion fluid; a waste receptacle; a plurality of fluid conduits defining: a delivery fluid path connecting the reservoir with the inlet; a return fluid path, independent of the delivery fluid path, connecting the reservoir with the outlet; and a waste fluid path connecting the reservoir with the waste receptacle; (iii) a first flow control device configured to selectively prevent or allow fluid flow from the reservoir to the organ via the delivery fluid path; and (iv) a second flow control device configured to selectively prevent or allow fluid flow from the reservoir to the waste receptacle via the waste fluid path.

BRIEF DESCRIPTIONS OF THE DRAWINGS

Embodiments are described with reference to the following figures, in which.

DETAILED DESCRIPTION OF THE EMBODIMENTS

Figure 1:
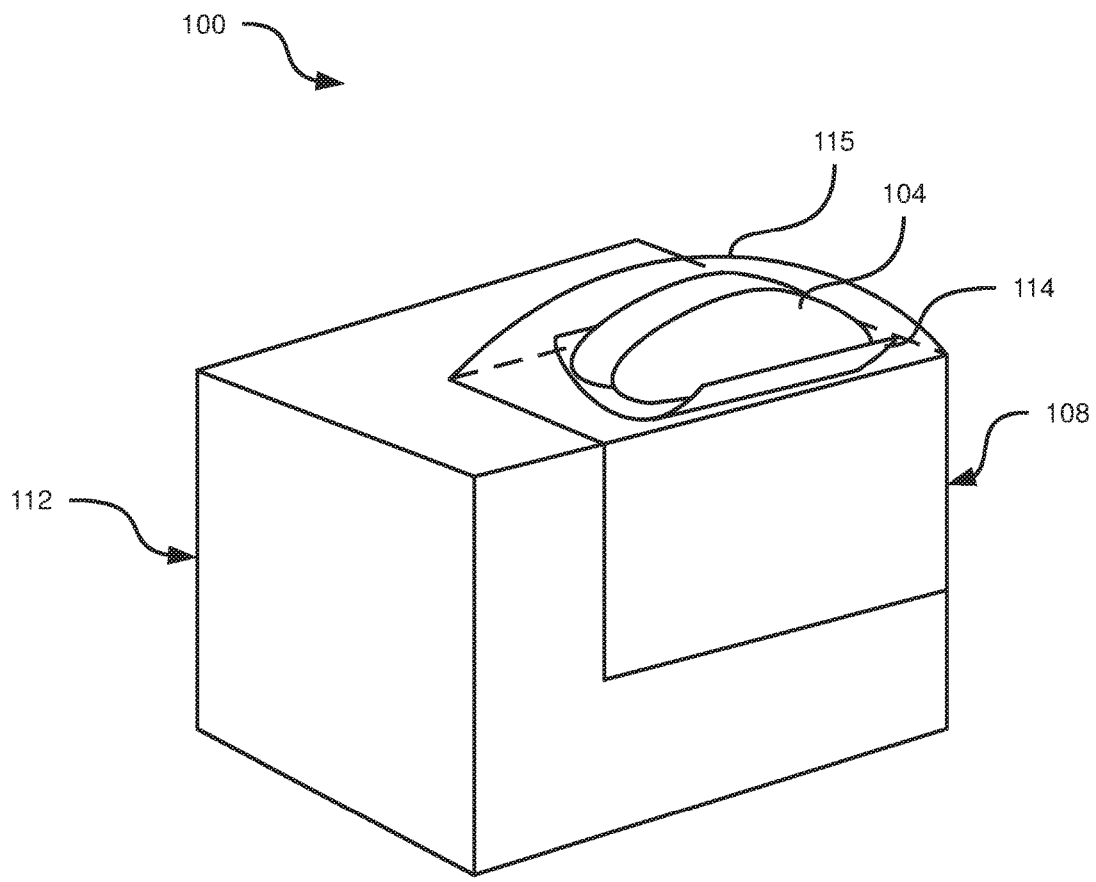
FIG. 1 depicts a perfusion device, according to a non-limiting embodiment.

FIG. 1 depicts an organ perfusion device 100, also referred to herein simply as device 100. Device 100, as will be described in greater detail below, is employed for at least one of evaluation, treatment and transportation of a donor organ 104, which in the present example is a pair of lungs (e.g. human lungs) collected from a donor and destined for implantation in a recipient patient (neither patient shown in FIG. 1). The discussion below is directed to the operation of device 100 for ex vivo perfusion; however, in other embodiments device 100 may also be employed for in vivo organ perfusion. As will be apparent throughout the discussion below, device 100 or variants thereof may also be employed with a variety of other organs including, for example, kidneys, hearts, and livers.

In general, device 100 is therefore configured to provide a substantially sterile environment for organ 104, by providing a compartment that substantially isolates organ 104 from the exterior of that compartment. Device 100 is also configured to permit perfusion of organ 104 with any suitable fluid (selected at least in part based on the nature of the organ being perfused) to enable the above-mentioned evaluation and treatment of organ 104, as well as to lengthen the available time for transportation of organ 104. When employed with some organs, such as lungs, device 100 is also configured to ventilate organ 104 with any suitable gas or mixture or gases to enable evaluation and treatment. When employed with other organs, device 100 may also be configured to remove fluids (e.g. urine for kidneys, bile for livers).

Further, as will be described below, device 100 is configured to be movable, for example from a donor site to a mode of transportation (e.g. an aircraft), and in turn from the mode of transportation to a recipient site (e.g. an operating room in a hospital). Still further, certain components of device 100 are disposable, while other components of device 100 can be reusable.

In the present example, device 100 includes a disposable assembly 108, and a reusable assembly 112. Disposable assembly 108 includes an organ support 114, such as a tray upon which organ 104 is placed, and also contains a perfusion circuit enabling the above-mentioned perfusion of organ 104. As will now be apparent to those skilled in the art, when device 100 is employed for in vivo perfusion of organ 104, organ support 114 need not be employed (and indeed, can be omitted). In such deployments of device 100, organ 104 is supported within the body of a patient, and no external organ support is therefore necessary. Disposable assembly 108 also includes a protective dome 115 (which need not be dome-shaped in other embodiments) that is connectable to an upper portion of disposable assembly 108 in order to provide a substantially sealed chamber to contain organ 104. The seal can be, but is not required to be, air-tight. Even if not air-tight, the seal is preferably water-tight. Disposable assembly 108 also includes a portion of a ventilation circuit, when a ventilation circuit is provided.

Reusable assembly 112 contains control equipment for the perfusion circuit, as well as other components to be discussed below in greater detail. Those other components can include the remainder of the ventilation circuit, when such a circuit is provided. The components of reusable assembly 112 are contained within a housing (e.g. having rigid walls and providing structural support for the components), which can include wheels or other locomotive means to permit movement of device 100.

Figure 2:
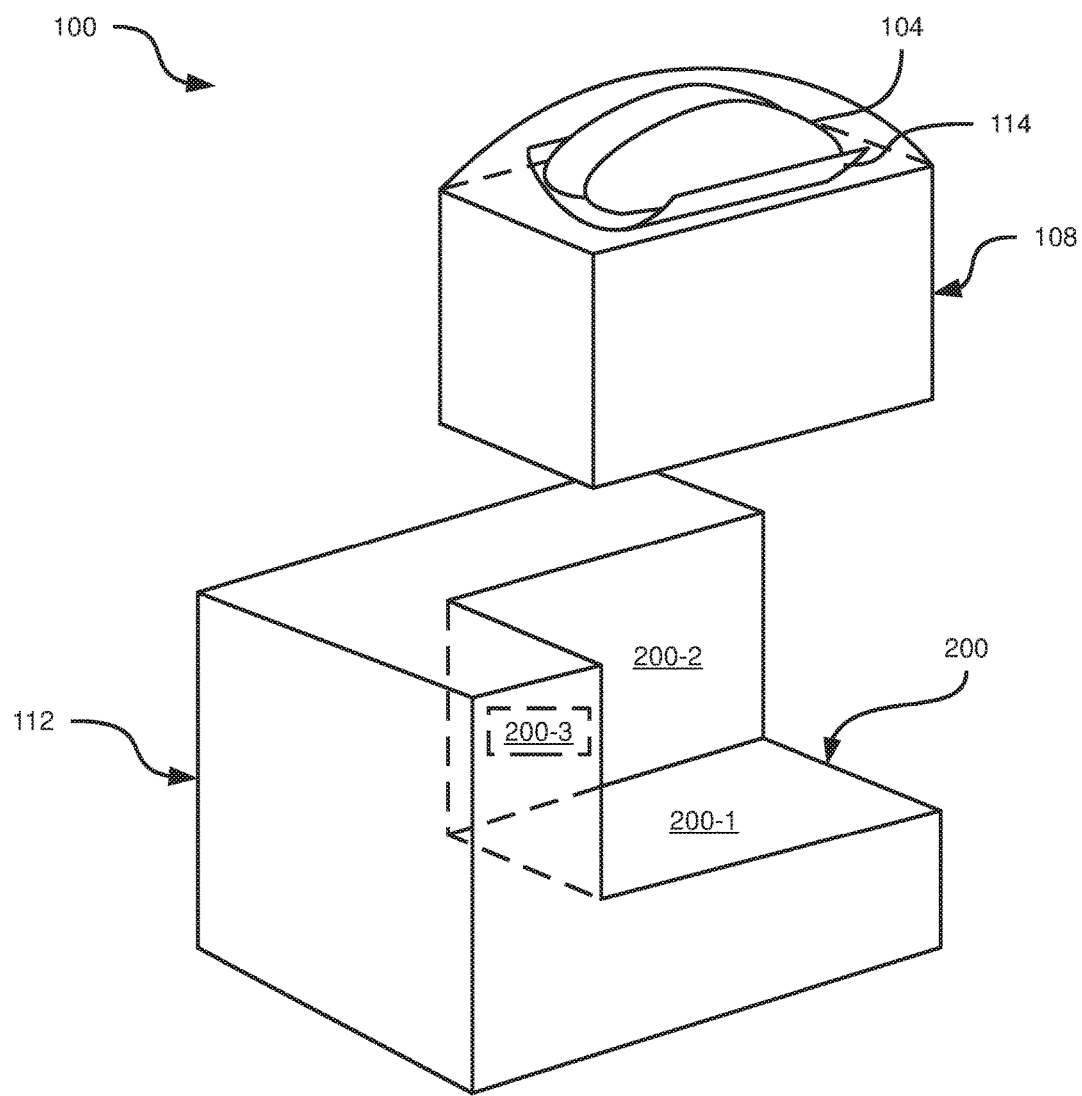
FIG. 2 depicts the perfusion device of FIG. 1, in a disassembled state, according to a non-limiting embodiment.

As seen in FIG. 2, disposable assembly 108 can be separated from reusable assembly 112, for example to transport reusable assembly 112 and organ 104 to the recipient site from the above-mentioned mode of transportation, or simply to remove and replace disposable assembly 108 after the removal of organ 104 therefrom (e.g. for implanting organ 104 in the recipient patient).

Reusable assembly 112 thus includes a dock 200 configured to releasably support disposable assembly 108 in an operational state (as seen in FIG. 1). Dock 200 can have a variety of structural arrangements. In the embodiment shown in FIGS. 1 and 2, dock 200 includes three interface surfaces 200-1, 200-2 and 200-3, which each come into contact with corresponding surfaces of disposable assembly 108 when device 100 is assembled in the operational state. A wide variety of other configurations may also be employed, however. For example, in other embodiments, dock 200 can include a single interface surface analogous to surface 200-1, for supporting disposable assembly 108 above reusable assembly 112. As will be apparent in the discussion below, the configuration of dock 200 depends in part on the arrangement of the physical connections between reusable assembly 112 and disposable assembly 108 to complete the ventilation circuit, to control the perfusion circuit, and to fulfill other functions of device 100.

Figure 3:
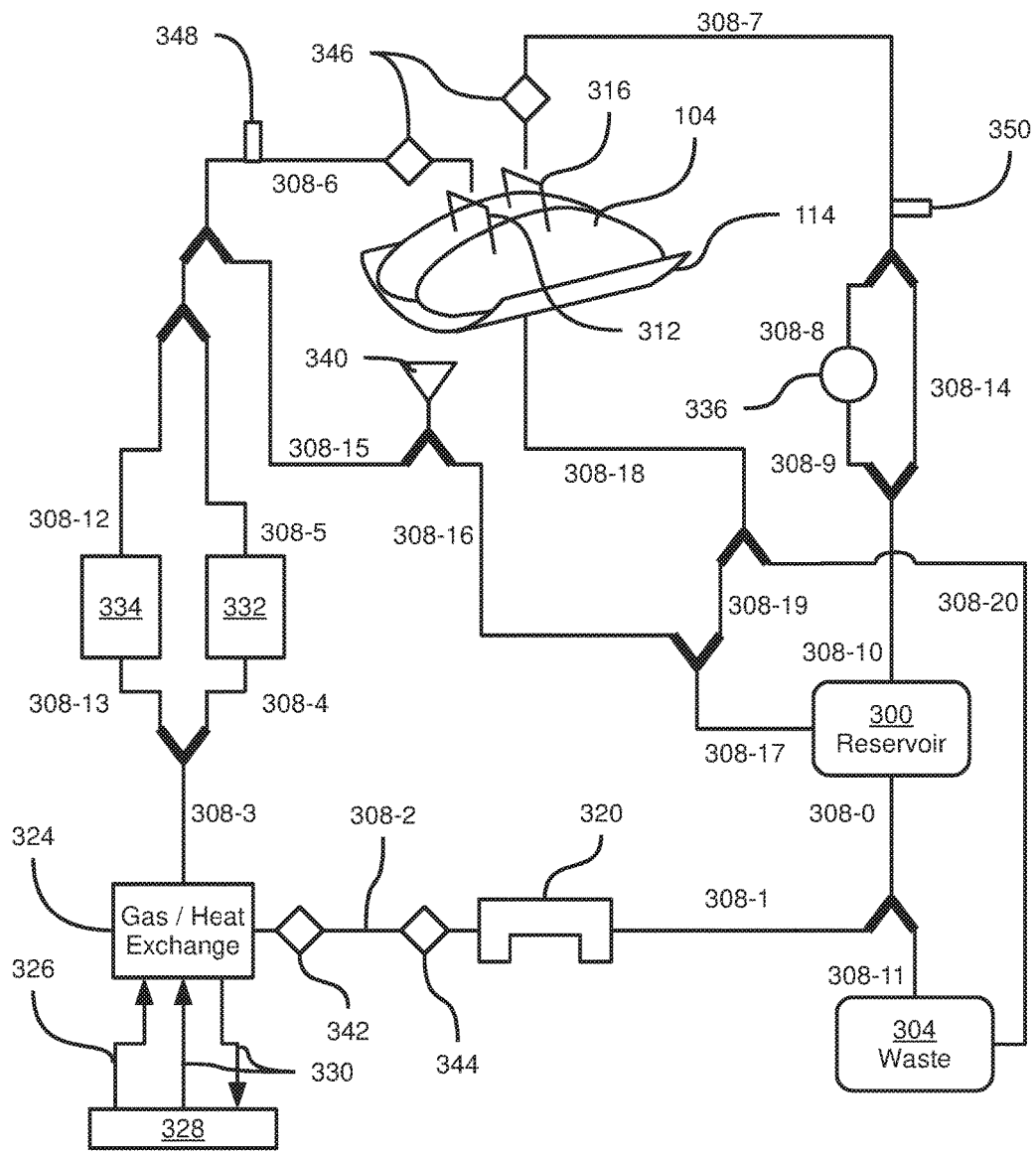
FIG. 3 depicts a perfusion circuit of the perfusion device of FIG. 1, according to a non-limiting embodiment.

As noted above, disposable assembly 108 includes a perfusion circuit. The perfusion circuit, in general, circulates a perfusion fluid between a reservoir and organ 104, in order to provide nutrients (e.g. glucose) to organ 104, evacuate metabolic by-products from organ 104, and optionally permit various evaluation and treatment activities to be performed with respect to organ 104. Turning now to FIG. 3, the perfusion circuit will be described in greater detail.

As seen in FIG. 3, the perfusion circuit includes a reservoir 300 configured to hold a perfusion fluid. The perfusion fluid can be any suitable fluid formulated to deliver nutrients and evacuate metabolic by-products to and from organ 104, respectively. In other embodiments, the perfusion fluid can be saline, water or the like, for example where nutrient delivery is not necessary but metabolic by-product evacuation is still desired. In the present example, the perfusion fluid is STEEN Solution™. Reservoir 300, as will be discussed in greater detail below, can have rigid or flexible walls (or any suitable combination thereof), made from any suitable biocompatible and impermeable material, such as plastic. The dimensions of reservoir 300 are dependent on the application of device 100. In the present example, in which device 100 is configured for the transportation of lungs, reservoir 300 can have an internal volume of about two liters. For other applications, however, as will now be apparent, a wide variety of other volumes may be suitable for reservoir 300.

The perfusion circuit also includes a waste receptacle 304 configured to receive the above-mentioned perfusion fluid under certain operational conditions, to be detailed below. Waste receptacle 304 can have any suitable shape and structure, including any suitable combination of flexible and rigid walls, made of any suitable impermeable material (e.g. plastics).

The perfusion circuit also includes a plurality of fluid conduits 308-0, 308-1, 308-2 and so on (collectively referred to as fluid conduits 308), such as lengths of flexible tubing (e.g. silicone, plastic, or the like) defining various fluid paths. In some embodiments, some or all of conduits 308 can be insulated, for example by being surrounded by larger-gauge tubing.

A fluid path, as referred to herein, permits the flow of fluid between two endpoints, through any suitable combination of the above-mentioned fluid conduits and other components. The fluid path is defined by the entire set of conduits 308 and other components along with the fluid flows between the two endpoints. Thus, for example, if two endpoints (e.g. reservoir 300 and waste receptacle 304) are connected by two sets of fluid conduits—even in the event that the two sets share certain fluid conduits—the endpoints are said to be connected by two different fluid paths.

The above-mentioned fluid paths include a delivery fluid path connecting reservoir 300 with an inlet 312 at organ support 114. Inlet 312 can be, for example, a cannula for connection with organ 104 for delivering perfusion fluid to organ 104. In the present example, in which organ 104 is a pair of lungs, inlet 312 is a cannula connected to the trunk of the pulmonary artery (or, in some embodiments, a pair of cannulae or a cannula with branching outlets connected respectively to the right and left pulmonary arteries). The delivery fluid path is defined, in the present example, by fluid conduits 308-0, 308-1, 308-2, 308-3, 308-4, 308-5 and 308-6, each representing a discrete length of tubing. It will now be apparent to those skilled in the art that a wide variety of other tubing configurations can be employed to define the delivery fluid path. The tubing configurations employed depend on the other components present in the delivery fluid path, as well as on the distance between components.

Fluid conduits 308 of the perfusion circuit also define a return fluid path connecting an outlet 316 at organ support 114 with reservoir 300. Outlet 316 can be, similarly to inlet 312, a cannula or pair of cannulae connecting fluid conduit 308-7 with either each of the left and right pulmonary veins of organ 104, or with the trunk of the pulmonary vein (which drains into the left atrium of the heart). The return fluid path is independent of the delivery fluid path—that is, the return fluid path and the delivery fluid path do not share any fluid conduits 308. As seen in FIG. 3, the return fluid path is defined by fluid conduits 308-7, 308-8, 308-9, and 308-10.

Fluid conduits 308 also define a waste fluid path connecting reservoir 300 with waste receptacle 304. As seen in FIG. 3, the waste fluid path is defined by fluid conduit 308-0 (shared with the above-mentioned delivery fluid path) and by fluid conduit 308-11. As will now be apparent to those skilled in the art, various other arrangements of fluid conduits 308 may be implemented to provide the above fluid paths (as well as those to be introduced below). For example, the waste fluid path need not share conduit 308-0 with the delivery fluid path. Instead, in embodiments in which reservoir 300 is provided with an outlet specific to the waste fluid path, conduit 308-11 can connect directly to reservoir 300 rather than branching from conduit 308-0.

The perfusion circuit can include a plurality of other components, and conduits 308 can define a plurality of additional fluid paths connecting various ones of those components. In particular, the perfusion circuit in the present embodiment includes a pump head module 320 located along the delivery fluid path. Pump head 320 drives fluid received from reservoir 300 (via conduits 308-0 and 308-1) towards inlet 312 (i.e. towards organ 104). More specifically, pump head 320 drives fluid to inlet 312 via a fluid conditioning module, such as a gas and heat exchange module 324.

In the present example, in which organ 104 is a pair of lungs, module 324 serves to de-oxygenate the perfusion fluid flowing through module 324 before the fluid is delivered to the lungs. De-oxygenation is achieved by the injection of carbon dioxide (or any other suitable mixture of gases) into the perfusion fluid. Carbon dioxide is received at module 324 via a gas supply line 326 connected to a mechanical interface 328 of disposable assembly 108. Module 324 is also configured to control the temperature of the perfusion fluid flowing therethrough, by way of a heat exchanger. In some embodiments, the heat exchanger is electrically powered. In the present embodiment, heat exchange is performed with heated fluid received at module 324, passed through a heat exchanger within module 324, and output from module 324, via input and output lines 330 connected to interface 328. As will be discussed in greater detail below, module 324 can be employed to heat the perfusion fluid to a target temperature (e.g. 37 degrees Celsius). In some embodiments, module 324 can also be operated to cool the perfusion circuit (e.g. via the operation of a thermo-electric cooler).

As will now be apparent, in other embodiments the gas exchange and heat exchange functions of module 324 can be performed by separate devices (e.g. an in-line electric heater can be provided upstream or downstream of a gas exchange module). In further embodiments, the gas exchange function may be omitted entirely, for example when organ 104 is an organ other than a lung or pair of lungs, that does not require gas exchange. In still further embodiments featuring the perfusion of organs other than lungs, the gas exchange function may be retained, albeit in a different form than discussed herein (e.g. to add oxygen to the perfusion circuit rather than carbon dioxide).

Also included along the delivery fluid path is a leukocyte filter 332 located downstream of module 324. Leukocyte filter, as will now be apparent to those skilled in the art, is configured to remove leukocytes from the perfusion fluid, which may otherwise accumulate in the perfusion fluid (causing inflammation in organ 104) as the fluid circulates through organ 104 and back to reservoir 300 for further circulation through organ 104.

The perfusion circuit can also include one or more additional leukocyte filters, such as a secondary filter 334. In some embodiments, secondary filter 334 can be omitted. In the present embodiment, however, secondary filter 334 is provided as an alternate to filter 332. Depending on the length of time that device 100 is in operation, filter 332 may become partially clogged with biological material, thereby placing greater stress on pump head 320 to continue driving the perfusion fluid to organ 104. Thus, it may be desirable to disable filter 332 and enable secondary filter 334. As will now be apparent, secondary filter 334 lies on an alternate delivery path from reservoir 300 to inlet 312, passing through the same conduits 308 as the delivery path, with the exception of conduits 308-4 and 308-5. Instead, the alternate delivery path is defined by conduits 308-12 and 308-13.

Other components of the perfusion circuit include a pressure control valve 336, for example a check valve, connected between conduits 308-8 and 308-9 (i.e. on the return fluid path). In other embodiments, pressure control valve 336 can be located entirely within a fluid conduit, and thus conduits 308-8 and 308-9 can be replaced with a single conduit. In general, pressure control valve 336 is configured to maintain a predetermined pressure level within conduits 308 (and therefore within the blood vessels of organ 104). For example, when organ 104 is a lung or pair of lungs, the predetermined pressure level is about 5 mm Hg, and thus the cracking pressure of check valve 336 is about 5 mm HG. As will now be apparent, when device 100 (or variants thereof) is employed for other organs, other perfusion fluid pressures may be desirable.

The perfusion circuit also includes an alternate, or secondary, return path from outlet 316 to reservoir 300. The alternate return path is defined by the same conduits as the above-mentioned return fluid path, with the exception of conduits 308-8 and 308-9, which are substituted by a fluid conduit 308-14. In other words, the alternate return path permits perfusion fluid to return to reservoir 300 while bypassing pressure control valve 336, as will be discussed below in greater detail.

The perfusion circuit includes several additional fluid paths. Included among those paths is a filter priming path connecting a priming port 340 with filters 334 and 332. Although priming port 340 (which may, for example, include a funnel) is illustrated below organ 104, it will now be apparent that the components of FIG. 3 are not shown in their true physical arrangement. In practice, port 340 is placed above all other components of the perfusion circuit, including inlet 312. The filter priming fluid path is defined by conduits 308-15, 308-5 and 308-12.

The fluid paths of the perfusion circuit also include a reservoir priming fluid path connecting port 340 with reservoir 300 and defined by conduits 308-16 and 308-17. It is contemplated that the connection between reservoir 300 and conduit 308-0 is unobstructed, and thus the reservoir priming path can also serve to prime pump head 320 and module 324, as will be discussed in greater detail (i.e. the reservoir priming path is not limited to priming only reservoir 300).

The fluid paths of the perfusion circuit also include an organ support return fluid path connecting organ support 114 with reservoir 300 via conduits 308-18, 308-19 and 308-17, as well as an organ support waste fluid path connecting organ support 114 with waste receptacle 304 via conduits 308-18 and 308-20. During the operation of device 100, fluid (both perfusion fluid and other biological fluids, such as blood) can leave organ 104 via the surface of organ 104 rather than outlet 316. Such fluid collects on organ support 114, which can be provided with one or more drains connected to conduit 308-18. The above-mentioned organ support return and waste paths allow such fluid to be, respectively, recycled into reservoir 300 or disposed of into waste receptacle 304. In some embodiments, one of the above paths can be omitted. For example, the organ support waste path can be omitted, and all fluid from organ support 114 can be directed to reservoir 300. As another example, the organ support return path can be omitted, and all fluid from organ support 114 can be directed to waste receptacle 304.

The perfusion circuit can also be equipped with one or more sensors and sampling ports. In the present example, flow and temperature sensors 342 and 344, respectively, are provided on the delivery fluid path. A controller (not shown) of device 100 can receive signals from sensors 342 and 344 in order to control the operation of pump head 320 and module 324 (or any other suitable heat exchanger provided instead of module 324). In addition, the perfusion circuit can include partial oxygen pressure sensors 346 near one or both of inlet 312 and outlet 316. Finally, sampling ports may be included upstream of inlet 312 (sampling port 348) and downstream of outlet 316 (sampling port 350), permitting the withdrawal of samples of perfusion fluid for testing outside device 100. In some embodiments, sampling ports 348 and 350 can be supplemented or replaced with additional in-line sensors, such as oxygen, carbon dioxide, and pH sensors.

Each of the components of the perfusion circuit that are interconnected by conduits 308 can include an air escape line (not shown), permitting air to escape those components during priming of the perfusion circuit (i.e. when the perfusion circuit is first supplied with perfusion fluid). In some embodiments, one or more air escape lines may be omitted. The physical arrangement of the components of the perfusion circuit and the relevance of the arrangement to priming will be discussed in greater detail below.

Device 100 also includes a plurality of flow control devices configured to selectively prevent or allow the perfusion fluid to flow the length of the above-mentioned fluid paths. That is, the above fluid paths can each be enabled or disabled by one or more flow control devices that interact with fluid conduits 308 to selectively block the flow conduits. Device 100 therefore has a plurality of operational states, each defined by which of the fluid paths are enabled, and which are disabled.

A variety of flow control devices may be employed in device 100. For example, inline valves may be placed within conduits 308. In the present example, however, the flow control devices are external to conduits 308, and thus do not contact the perfusion fluid. Moreover, in the present embodiment the flow control devices are located in reusable assembly 112 and brought into contact with the appropriate conduits 308 when disposable assembly 108 is installed within dock 200.

Figure 4:
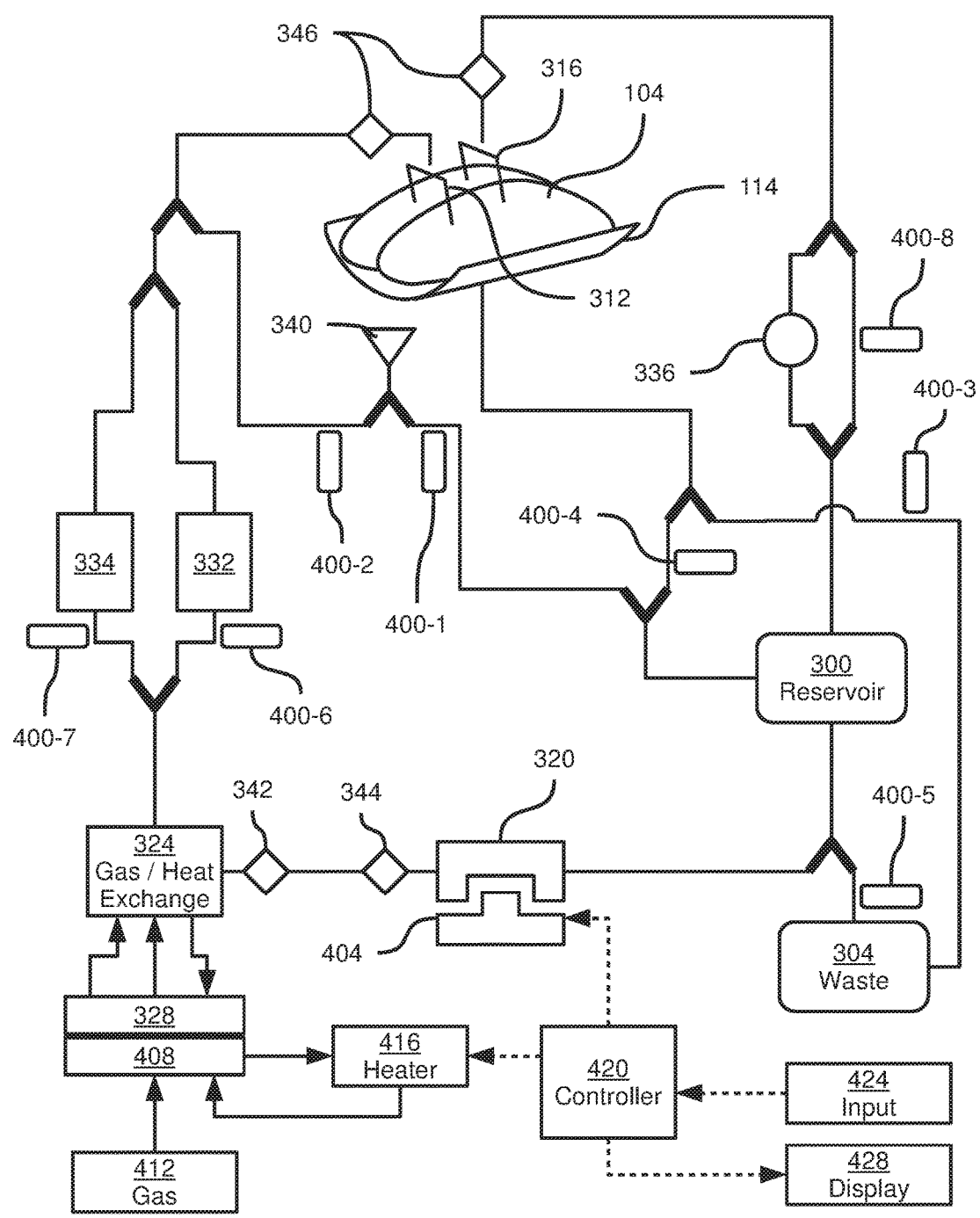
FIG. 4 depicts the perfusion circuit of FIG. 3 with certain additional components of the perfusion device of FIG. 1, according to a non-limiting embodiment.

Turning now to FIG. 4, the perfusion circuit (which, as noted earlier, is housed in disposable assembly 108 in the present embodiment) is illustrated along with certain components of reusable assembly 112, including a plurality of flow control devices 400. In particular, in the present embodiment, eight flow control devices 400-1, 400-2, 400-3, 400-4, 400-5, 400-6, 400-7 and 400-8 are shown. In other embodiments, other fluid conduit configurations can be deployed that require a different number and arrangement of flow control devices 400 to place device 100 in the operational states to be discussed below.

Other components of reusable assembly 112 are also illustrated in FIG. 4, including a pump drive module 404 for actuating pump head 320. Reusable assembly 112 also includes a complementary mechanical interface 408 configured to mate with interface 328 of disposable assembly 108 and connect, via fluid or gas lines as appropriate, a perfusion gas source 412 and a heating fluid source (also referred to simply as a heater) 416 with module 324. In addition, reusable assembly 112 includes a controller 420 interconnected with pump drive 404, heater 416, as well as an input device (e.g. keyboard, mouse, touch screen, keypad or the like) 424 and a display 428 (e.g. an LCD screen or the like, which in some embodiments can be integrated with the above-mentioned input device 424, when input device 424 includes a touch screen).

Controller 420 is also connected, either wirelessly or via wired connections (not shown) with sensors 342, 344 and 346. When such connections are wired, it will now be apparent that the connections can travel through interfaces 408 and 328, or through any suitable number of other complementary mechanical interfaces carrying electrical contacts. Controller 420 is also connected to each of the above-mentioned flow control devices 400, for setting each device 400 in either an open or closed position, as will be described below in greater detail. The connections between controller 420 and devices 400 can also be any suitable combination of wired and wireless connections.

Controller 420 can be implemented as any suitable microcomputer, including one or more integrated circuits, such as a processor (also referred to as a central processing unit, or CPU) connected with a non-transitory computer readable storage medium in the form of a memory (non-volatile, volatile, or a combination thereof).

Reusable assembly 112 also contains a power source (e.g. one or more batteries or any other suitable source of electrical power). The power source supplies electrical power to controller 420, input device 424, display 428, as well as any other electrically-powered components. In the present example, flow control devices 400 are electrically-powered, as are pump drive 404 and certain components of module 324 (e.g. the above-mentioned thermo-electric cooler).

Figures 5A, 5B:
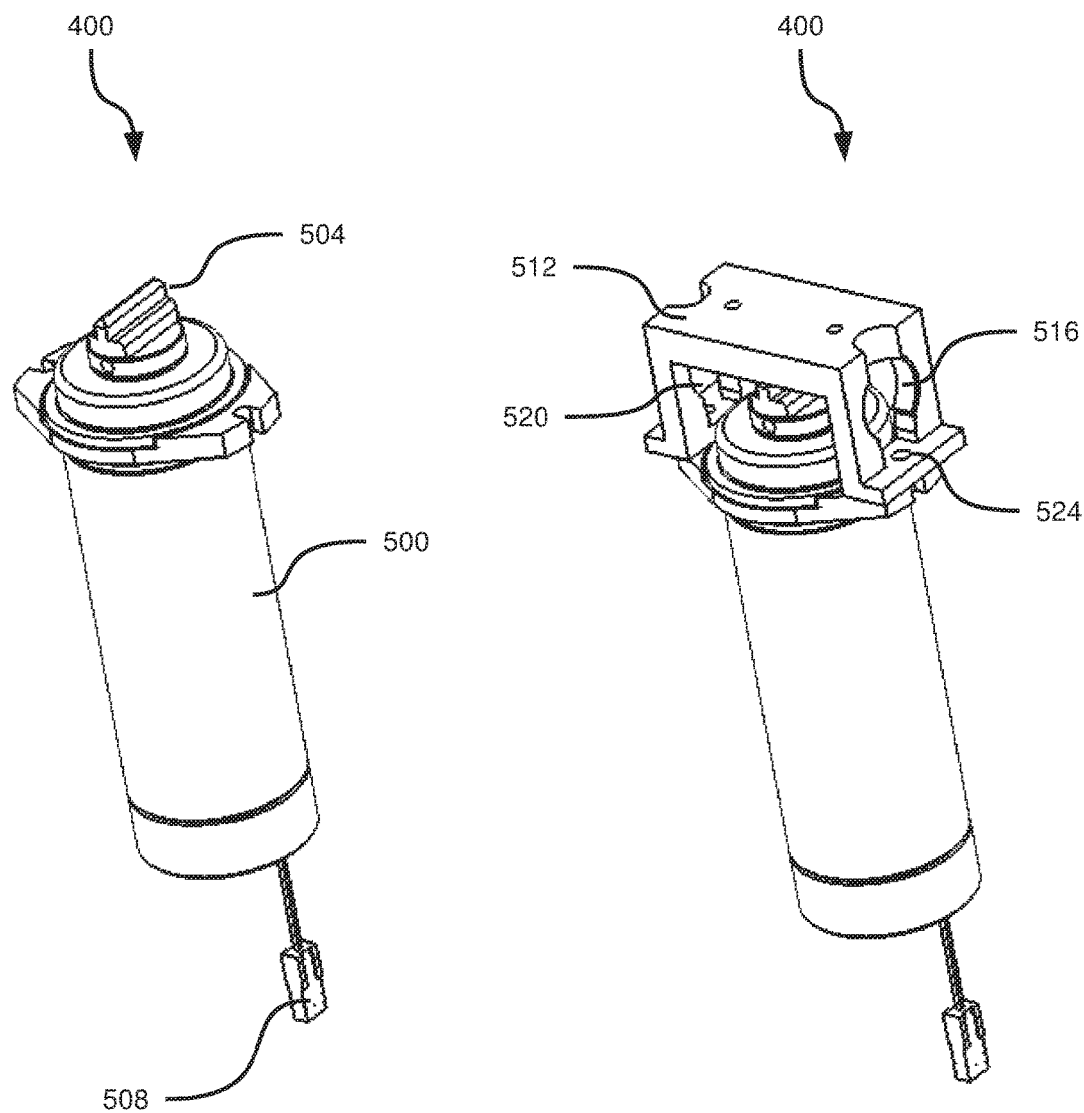
FIGS. 5A and 5B depict a flow control device of the perfusion device of FIG. 1, according to a non-limiting embodiment.

Before further discussion of the operation of flow control devices 400, the structure of flow control devices 400 will be described in further detail. Turning to FIG. 5A, a flow control device 400 is illustrated in isolation. Flow control device 400 includes a body 500 housing a solenoid assembly configured to drive a shaft (not shown) bearing a head 504 between open and closed positions. Head 504 is configured to abut a fluid conduit 308. Thus, in the open position, the distal ridge of head 504 is aligned with fluid flow through the corresponding conduit 308, and thus fluid flow is permitted. In the closed position, the ridge is aligned at a substantially right angle to the fluid flow, and thus blocks fluid flow. Flow control device 400 also includes, in embodiments using wired connections, at least one electrical connection 508 carrying power and control signals to flow control device 400.

FIG. 5B illustrates flow control device 400 with a bracket 512 mounted to body 500 adjacent to head 504. Bracket 512 includes opposing openings 516, 520 through which a fluid conduit 308 passes. Bracket 512 also includes locating structures, such as apertures 524, for locating bracket 512 against body 500. Bracket 512, in the present embodiment, is a component of disposable assembly 108, and is fixed to a fluid conduit 308 at a location requiring flow control. Such locations are selected such that when disposable assembly 108 is placed on dock 200, brackets 512 each come into contact (correctly located by, for example, apertures 524) with a flow control device 400. Thus, the heads 504 of the flow control devices 500 abut fluid conduits 308, and either permit flow through such conduits or prevent flow through such conduits.

In the event that a flow control device 400 loses electrical power, it fails to a predetermined position (i.e. either to open or close its corresponding fluid conduit 308). As will be seen below, the predetermined failure positions of flow control devices 400 together define a fail-safe operational state for device 100, in the event of a malfunction such as a loss of power.

Returning to FIG. 4, as noted above, each flow control device selectively prevents or allows fluid flow via one of the fluid paths described earlier. Specifically, device 400-1 controls flow via the reservoir priming fluid path; device 400-2 controls flow via the filter priming fluid path; device 400-3 controls flow via the organ support waste fluid path; device 400-4 controls flow via the organ support return fluid path; device 400-5 controls flow via the waste fluid path; device 400-6 controls flow via the delivery fluid path; device 400-7 controls flow via the alternate delivery fluid path; and device 400-8 controls flow via the alternate return fluid path.

Flow control devices 400 can be individually controlled to enable or disable any of a wide variety of combinations of the above-mentioned fluid paths. Each combination of enabled (and therefore also of disabled) fluid paths is referred to as an operational state of device 100. In the present example, controller 420 is configured to store a plurality of operational states each defined by a set of positions for flow control devices 400. Controller 420 is further configured, based on either input data received (e.g. from an operator of device 100) via input device 424, or on an automatic determination performed by controller 420 itself (e.g. based on data received from the above-mentioned sensors), to select one of the stored operational states, and to transmit control signals to flow control devices 400 to effect that operational state.

In other embodiments, the storage of operational states and corresponding flow control device 400 positions by controller 420 can be omitted. Instead, in such embodiments, controller 420 can be configured to receive input data from input device 424 specifying the position of each flow control device 400 individually. That is, the operator of device 100 in such embodiments is responsible for not only selecting the operational state, but also for instructing controller 420 as to the position of each flow control device 400 individually. In further embodiments, the above modes of operation (i.e. operational state storage by controller 420, and manual operational state management by an operator) can be combined. For example, controller 420 can store and implement operational states as described above, but can also be responsive to a predetermined input from input device 424 in order to switch to manual operational state management, permitting an operator of device 100 to exert greater control over device 100 (e.g. to place device 100 in an operational state not stored by controller 420).

Table 1 depicts a plurality of operational states—eight, in particular—for device 100, and the corresponding positions of each flow control device 400. Controller 420 can store the operational states of Table 1 (or, indeed, any other desired operational states) in any suitable format, including but not limited to the tabular format shown below.

TABLE 1

Flow Control Device Settings Defining Operational States

| State | Flow Ctrl. Device | | | | | | | |
|---|---|---|---|---|---|---|---|---|
| | 400-1 | 400-2 | 400-3 | 400-4 | 400-5 | 400-6 | 400-7 | 400-8 |
| Priming | Open | Open | Close | Close | Close | Open | Open | Open |
| Perfusion | Close | Close | Close | Open | Close | Open | Close | Close |
| Alternate Perfusion | Close | Close | Close | Open | Close | Close | Open | Close |
| Fluid Removal | Close | Close | Close | Open | Open | Prev. | Prev. | Close |
| Fluid Replenish | Open | Close | Close | Open | Close | Prev. | Prev. | Close |
| Terminate | Close | Open | Close | Open | Open | Close | Close | Open |

TABLE 1-continued

Flow Control Device Settings Defining Operational States

| State | Flow Ctrl. Device | | | | | | | |
|---|---|---|---|---|---|---|---|---|
| | 400-1 | 400-2 | 400-3 | 400-4 | 400-5 | 400-6 | 400-7 | 400-8 |
| Emerg. Failure | Close | Open | Close | Close | Open | Close | Close | Open |
| Tray Fluid Removal | Close | Close | Open | Close | Close | Prev. | Prev. | Close |

As seen above, each operational state specifies a position for each fluid control device 400, and thus enables or disables each of the above-mentioned fluid paths. Some operational states do not require a specific position for certain flow control devices 400, and therefore allow those flow control devices 400 to remain in their previous positions. For example, the fluid replenishment operational state does not require a particular position for either of flow control devices 400-6 and 400-7. Therefore, when the operational state of device 100 transitions from a previous state to the fluid replenishment state, the position of flow control devices 400-6 and 400-7 does not change.

As noted above, flow control devices 400 fail to predetermined positions, for example in the event of a loss of power. The emergency failure operational state above indicates the failure positions of each flow control device 400. In other words, the emergency failure operational state need not be (although it can be) positively selected by controller 420 or an operator of device 100. Instead, the emergency failure operational state can become active simply by virtue of a power loss to device 100. The "emergency failure" state shown above can be activated automatically by virtue of the fail-safe positions of flow control devices 400, or can be activated manually by an operator of device 100, in order to protect the organ(s) in device 100 in response to any failure of either or both of device 100 or a procedure being performed with device 100.

Figure 6:
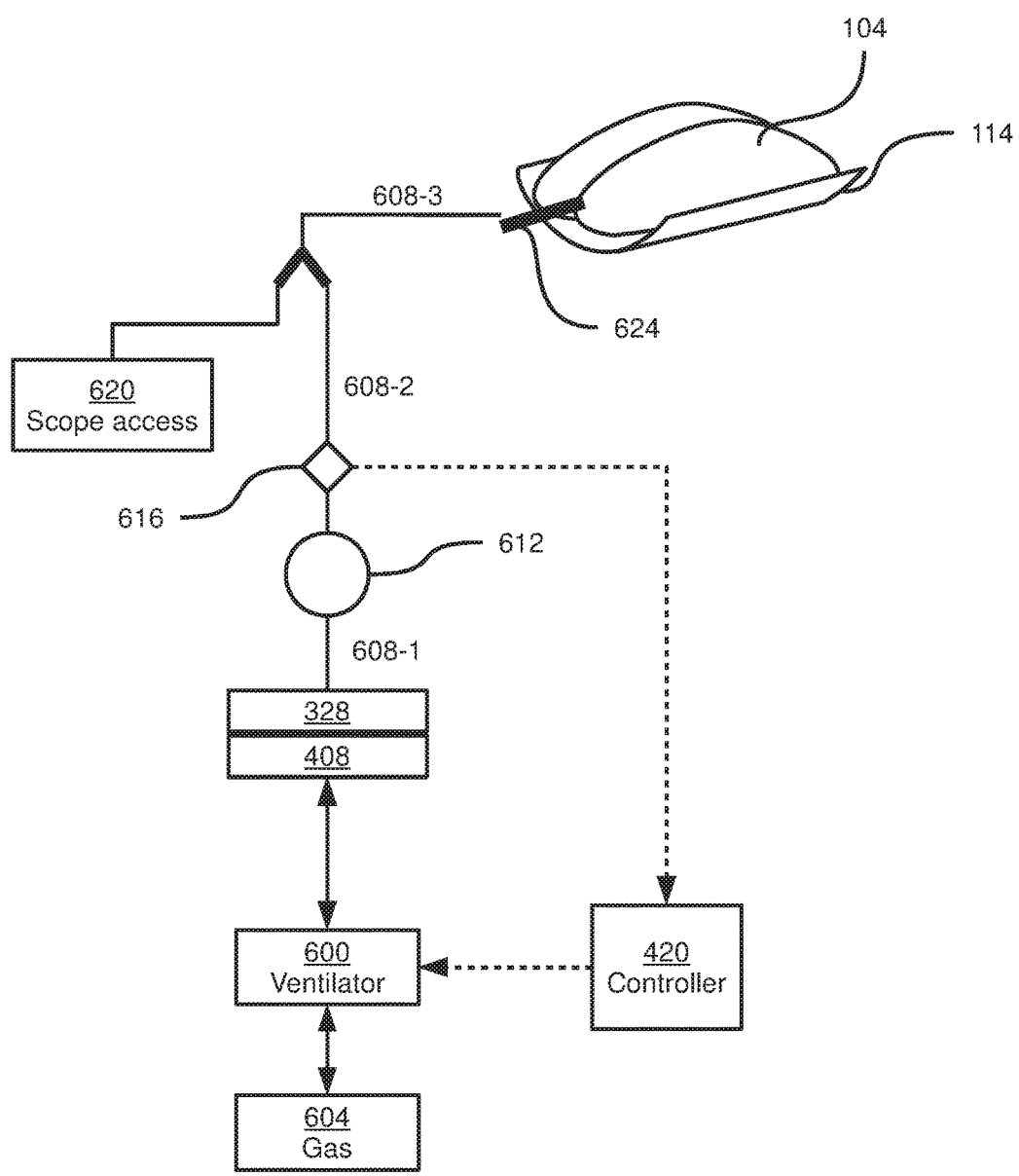
FIG. 6 depicts a ventilation circuit of the perfusion device of FIG. 1, according to a non-limiting embodiment.

Prior to a further discussion of the operation of the perfusion circuit, additional components of device 100 will be described below. In particular, as noted above, device 100 in the present embodiment is configured for the transport and treatment of lungs, and therefore includes a ventilation circuit in addition to the perfusion circuit. The components of the ventilation circuit are illustrated in FIG. 6. Although FIG. 6 omits the perfusion circuit for visibility, it will be apparent that both the ventilation circuit and the perfusion circuit are contained within device 100.

The ventilation circuit, in general, is configured to connect organ 104 with a ventilator 600 (e.g. bellows) supplied with gas, such as pure oxygen, atmospheric air, or the like, from a gas supply 604. Ventilator 600 and gas supply 604 are contained within reusable assembly 112, and interface with gas conduits 608 (conduits 608-1, 608-2 and 608-3 are shown, but any combination of conduits can be employed to deliver gases to and from organ 104). The interface between the ventilator and conduits 608 is provided, in the present embodiment, by mechanical interfaces 328 and 408, discussed earlier in connection with the perfusion circuit. That is, interfaces 328 and 408 can carry connections for both the perfusion circuit and the ventilation circuit. In other embodiments, separate mechanical interfaces may be provided on disposable assembly 108 and reusable assembly 112 for the ventilation and perfusion circuits.

The ventilation circuit includes an exhaust valve 612 as well as a flow sensor 616, which can be connected wirelessly or via a wired connection to controller 420. In some embodiments, the flow sensor 616 is implemented as one or more pitot tubes. Further, the ventilation circuit can include a bronchoscopy access port 620 connected to conduit 608-3 to permit inspection of the lungs. Conduit 608-3, in turn, is connected to a tracheal tube 624 for connection to the trachea. The ventilation circuit can also include one or more conditioning devices (e.g. heat and moisture exchangers), to control the temperature and moisture content of the gas delivered to organ 104. In the present example, such conditioning devices are contained in disposable assembly 108, as they generally also contain disposable air filters. In other embodiments, certain conditioning devices (e.g. humidifiers) may be reusable, and therefore housed in reusable assembly 112.

Figure 7:
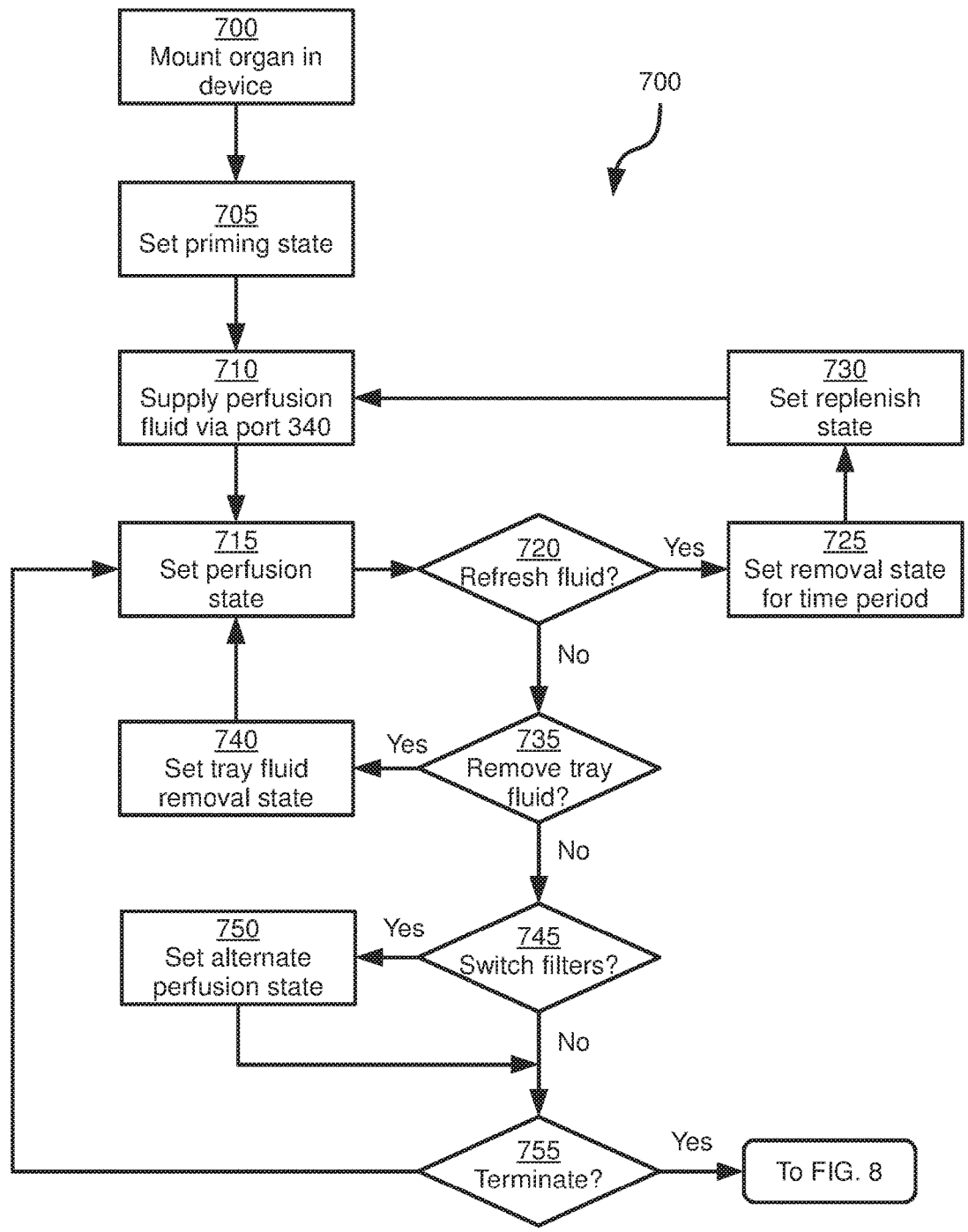
FIG. 7 depicts a method of operation of the perfusion device of FIG. 1, according to a non-limiting embodiment.

Having described the internal components of device 100, the operation of device 100 will now be discussed. FIG. 7 depicts a method 700 of initializing and operating device 100. At block 700, organ 104 is mounted in device 100. That is, when organ 104 is a lung or pair of lungs, the lungs are placed on organ support 114, the trachea is connected to the ventilation circuit, and the pulmonary arteries and veins are connected to the perfusion circuit. Dome 115 is then placed over the lungs.

At block 705, the perfusion circuit is set to the priming state, as shown above in Table 1. As noted earlier, the selection of an operational state can be performed by controller 420 responsive to receiving input data identifying the operational state from input device 424. At block 710, perfusion fluid is supplied to the perfusion circuit via priming port 340. As will now be apparent from FIG. 4 and Table 1, the perfusion fluid supplied at block 710 travels into reservoir 300 and subsequently through pump head 320, module 324 and into filters 334 and 332. The supplied fluid also travels (via conduits 308-15, 308-5 and 308-12) to filters 334 and 332 against the normal direction of fluid flow, to ensure complete priming of filters 334 and 332. Following supply of the perfusion fluid (in the present embodiment, about two liters is supplied, although other volumes may also be supplied, depending on the type and size of organ 104), the performance of method 700 proceeds to block 715.

At block 715, the perfusion circuit is set to the perfusion operational state as shown in Table 1. When, as in the present embodiment, a ventilation circuit is included in device 100, the ventilation circuit is also activated at block 715. In addition, pump drive 404 is activated at block 715. As a result, perfusion fluid is driven from reservoir 300 via the delivery fluid path to organ 104, and fluid leaving organ 104 at outlet 316 is driven back to reservoir 300 via the return fluid path.

At block 720, a determination is made as to whether to refresh the perfusion fluid in device 100. In some embodiments, block 720 (as well as blocks 725 and 730, to be discussed below) can be omitted. In the present embodiment, however, certain ex vivo lung perfusion protocols contemplate the removal and replacement of a certain amount of perfusion fluid at predefined time intervals (e.g. 500 mL after the first hour of operation, and 250 mL every hour of operation thereafter). Refreshing the perfusion fluid dilutes any metabolic by-products that may have accumulated in reservoir 300, and replenishes the supply of nutrients (particularly glucose) in the perfusion fluid. Refreshing the perfusion fluid may also dilute hormonal compounds (e.g. generated by immune cells in the organ) therein, which may otherwise cause undesirable inflammation.

When the determination at block 720 is affirmative, the performance of method 700 proceeds to block 725, at which the perfusion circuit is set to the fluid removal state until the desired volume of perfusion fluid has been transferred to waste receptacle 304 (e.g. for a predetermined length of time, selected based on a known flow rate along the waste fluid path, or selected based on a visual assessment of fluid level in waste receptacle 304 by an operator of device 100). It will be apparent from Table 1 (as well as FIGS. 3 and 4) that during the performance of block 725, the circulation of perfusion fluid from reservoir 300 through organ 104 and back to reservoir 300 continues.

At block 730, following the removal of a predetermined volume of perfusion fluid from reservoir 300 to waste receptacle 304, device 100 is set to the fluid replenishment operational state at block 730, and a corresponding volume of perfusion fluid is supplied via priming port 340 in a further performance of block 710. In some embodiments, the corresponding volume of perfusion fluid supplied via priming port 340 at block 730 is equal to the volume of perfusion fluid directed to waste receptacle 304 at block 725. In other embodiments, however, a greater or smaller volume of fluid may be supplied at block 730 than was removed at block 725. The performance of method 700 then resumes at block 715.

Following a negative determination at block 720, at block 735 a determination is made as to whether to remove fluid from organ support 114 from circulation. It may be desirable to remove fluid from organ support 114 rather than recycle that fluid into reservoir 300 under certain circumstances, such as early in the operation of device 100, when other biological fluids (e.g. blood) are more likely to be present in runoff collected by organ support 114. When the determination at block 735 is affirmative, the perfusion circuit is set to the tray fluid removal operational state for a selectable period of time (during which regular circulation of perfusion fluid to organ 104 continues, and fluid from organ support 114 drains to waste receptacle 304 via the above-mentioned organ support waste fluid path connecting organ support 114 with waste receptacle 304 via conduits 308-18 and 308-20), following which the perfusion circuit is returned to the perfusion state at block 715. As will now be apparent, the determinations at blocks 720 and 735 can occur in the reverse order from that shown in FIG. 7. Similarly, the performance of blocks 745 and 755, to be discussed below, need not occur in the order shown.

Following a negative determination at block 735, at block 745 a determination is made as to whether to switch from one leukocyte filter (e.g. filter 332) to another (e.g. filter 334). When the determination is affirmative, the perfusion circuit is set to the alternate perfusion state, which (as evidenced in Table 1) redirects the flow of perfusion fluid from the delivery fluid path to the alternate delivery fluid path at block 750, leaving the state of the remaining fluid paths unchanged. When two leukocyte filters are provided, as in the present embodiment, the operation of device 100 may be referred to as having two stages: a "ramp-up" stage in which a first filter is employed, and a "normal" stage in which the second filter is used.

When the determination at block 745 is negative, at block 755 a determination is made as to whether or not to terminate operation of device 100. An affirmative decision may be reached at block 755 because device 100 has reached its destination and organ 104 must be prepared for implantation into a recipient patient. In other scenarios, the determination at block 755 may be an unplanned termination, for example as a result of a component failure, loss of power or the like. When the determination at block 755 is negative, the performance of method 700 continues at block 715.

Figure 8:
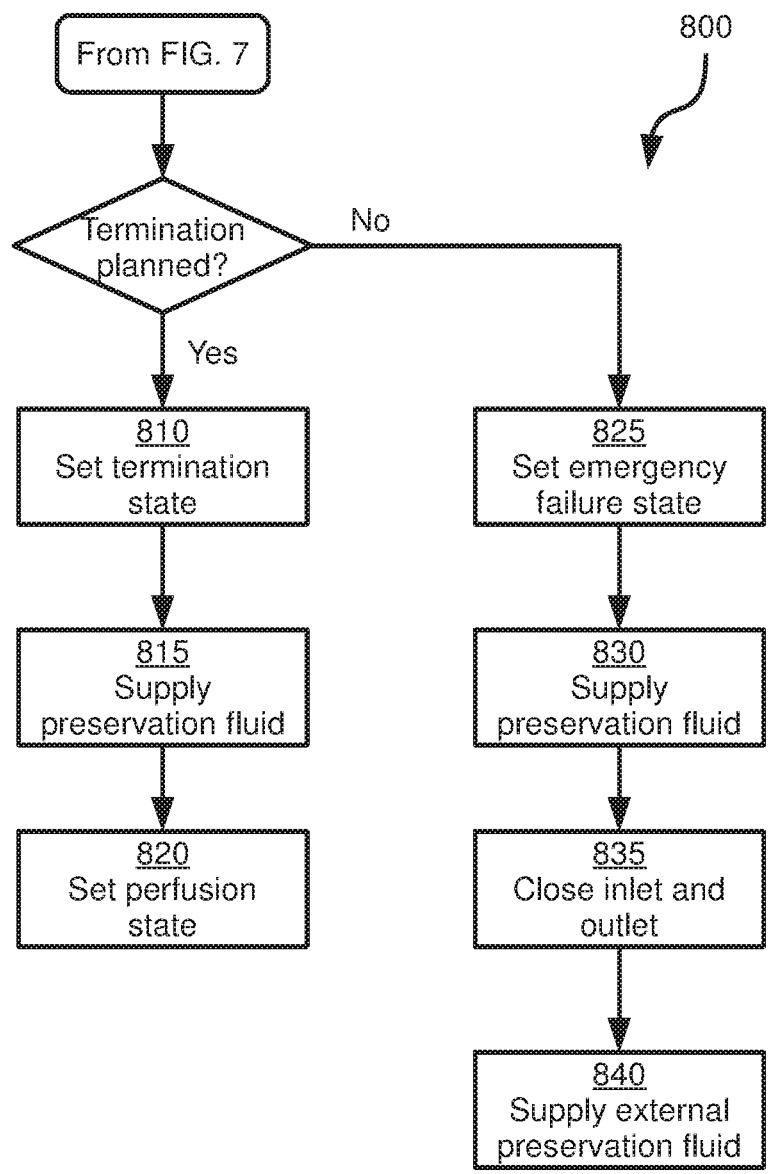
FIG. 8 depicts a method of terminating operation of the perfusion device of FIG. 1, according to a non-limiting embodiment.

When the determination at block 755 is affirmative, however, the operation of device 100 continues as depicted in FIG. 8.

FIG. 8 depicts a method 800 of terminating the operation of device 100. The performance of method 800 varies depending on whether the termination is planned (i.e. does not result from a malfunction) or unplanned (i.e. does result from a malfunction of device 100). When the termination is planned, for example following the successful transportation of organ 104 to a destination site for implantation into a recipient patient, the goal of the termination process is to reduce the metabolic rate of organ 104 to preserve organ 104 while the recipient patient is prepared for implantation.

At block 810, the perfusion circuit is placed in the termination state shown in Table 1. As seen in Table 1, in the termination state, the delivery fluid path is interrupted (both filters 332 and 334 are blocked from receiving perfusion fluid), and all remaining perfusion fluid in the perfusion circuit is permitted to flow through reservoir 300 into waste receptacle 304. Additionally, the operation of pump drive 404 is interrupted, and the ventilation circuit may also be disabled (e.g. by turning off ventilator 600 and closing tracheal tube 624 with a clamp or other suitable implement). At block 815, during the draining of the perfusion circuit initiated at block 810, preservation fluid (preferably cooled preservation fluid, e.g. Perfadex™) is supplied to the perfusion circuit via priming port 340.

Following the introduction of preservation fluid, circulation of the preservation fluid may be resumed at block 820 by returning the perfusion circuit to the perfusion state (and therefore enabling pump drive 404). In addition, the heat exchanger of module 324 can be switched from a heating function to a cooling function. For example, when organ 104 is a lung or pair of lungs, it is desirable to maintain the preservation fluid at a temperature of about ten degrees Celsius. As will now be apparent, when the recipient is ready to receive organ 104, a final termination stage may be initiated, by repeating the performance of block 810, but without performing blocks 815 or 820.

When the operation of device 100 is terminated in an unplanned manner (e.g. due to power loss or component failure), at block 820 the perfusion circuit is placed in the emergency failure state, either by input from an operator or by virtue of the failure positions of flow control devices 400. At block 830 preservation fluid is supplied to the perfusion circuit, as described above in connection with block 815. At block 835, inlet 312 and outlet 316 are closed (e.g. with clamps, covers or the like) to retain some preservation fluid within organ 104. Further, at block 840, additional preservation fluid may be supplied to dome 115 via a cap (not shown) in dome 115, such that the exterior of organ 104 is surrounded at least partly by preservation fluid.

Figure 9:
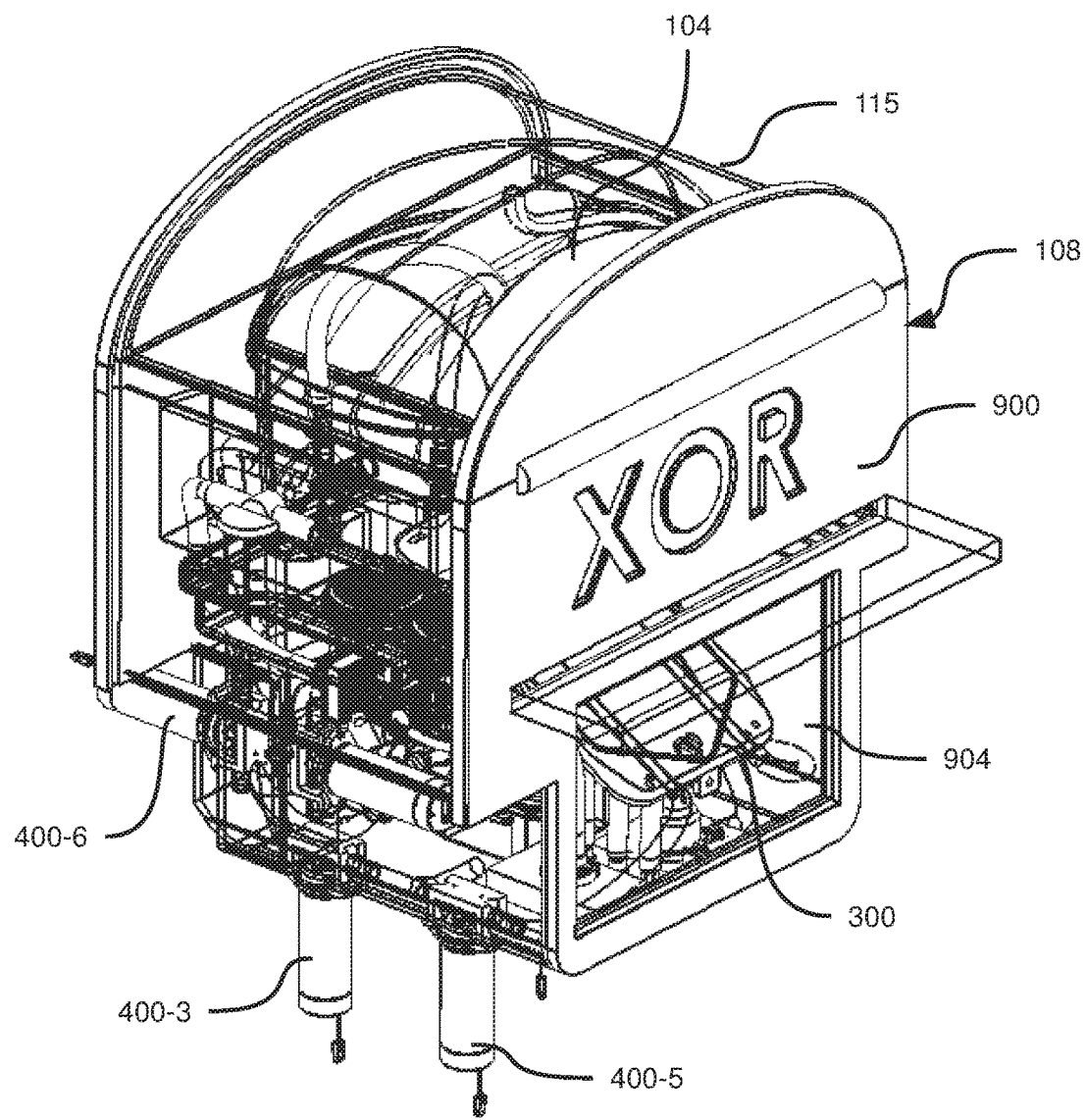
FIG. 9 depicts an example implementation of the perfusion circuit of FIG. 3, according to a non-limiting embodiment.

Having described the components and operation of device 100, the structure of certain components, as well as an example arrangement of those components, of device 100 will be described. Referring now to FIG. 9, an example implementation of disposable assembly 108 is illustrated. As seen in FIG. 9, assembly 108 includes a housing 900 supporting organ 104 (on a tray, not shown) and carrying dome 115. Housing 900 may include a window 904 permitting reservoir 300 to be viewed therethrough. In addition to certain components of assembly 108, flow control devices 400 are also visible in FIG. 9, although as noted above, they are preferably mounted within reusable assembly 112 (not shown) in order to contact disposable assembly 108 when assembly 108 is docked. As will be apparent in the drawings discussed below, flow control devices 400 may protrude from reusable assembly 112 on all three of surfaces 200-1, 200-2 and 200-3.

Figure 10A:
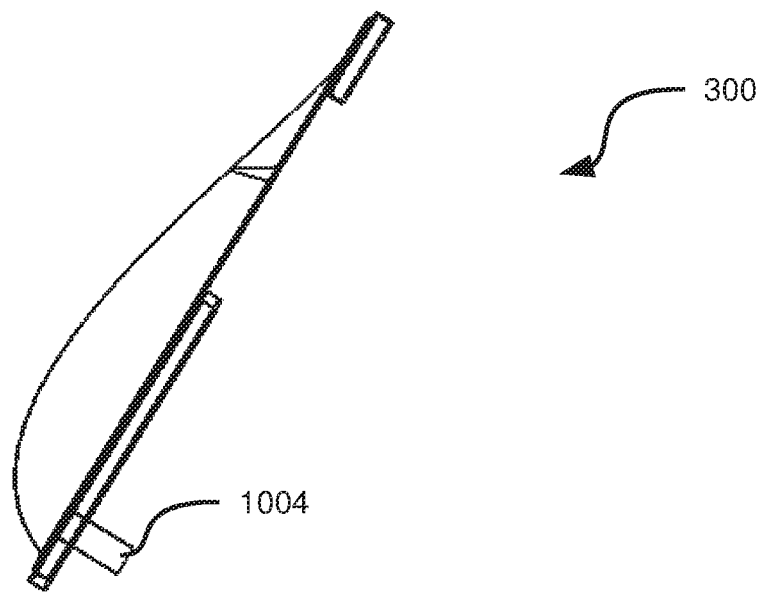
FIGS. 10A and 10B depict a reservoir of the perfusion circuit of FIG. 3, according to a non-limiting embodiment.
Figure 10B:
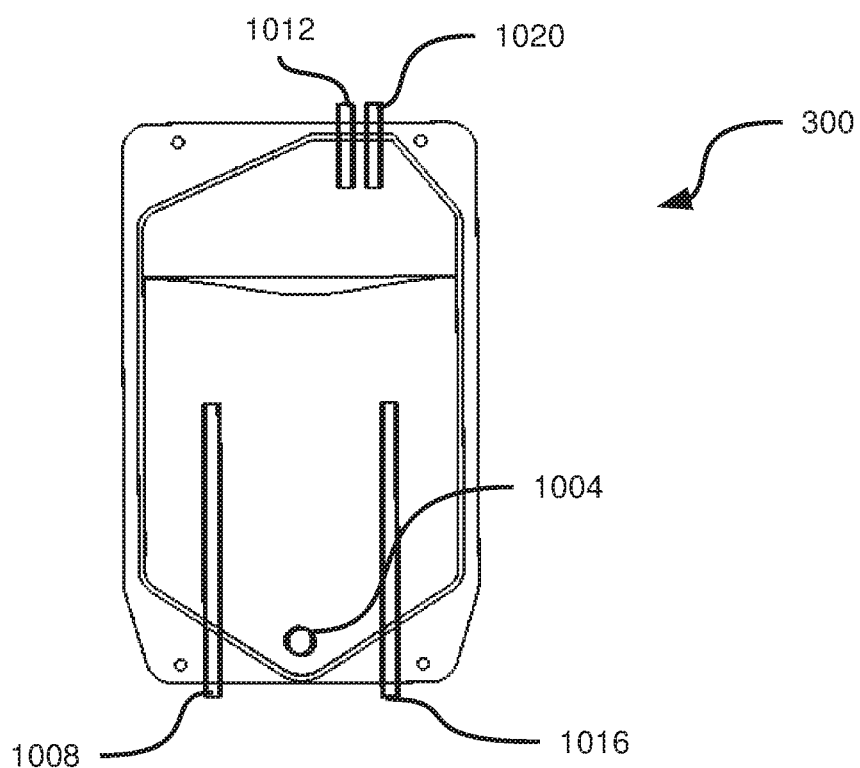

Referring now to FIGS. 10A and 10B, side and front views of reservoir 300 are shown. As seen in FIGS. 10A and 10B, reservoir 300 can include a plurality of inlets and outlets, based on the configuration of conduits 308 that are connected to reservoir 300. In the present example, reservoir 300 is a flexible bag (e.g. made of any suitable plastic material) that includes an outlet 1004 connecting to conduit 308-0, as well as an outlet 1008 connecting reservoir 300 to waste receptacle 304 (that is, in the embodiment of FIG. 10, conduit 308-0 is replaced with two distinct conduits). Reservoir 300 also includes an inlet 1012 for receiving perfusion fluid from priming port 340 or from organ support 114, as shown in FIG. 3. A further inlet 1016 receives perfusion fluid via the return fluid path (that is, returning from organ 104), and an air escape port 1020 permits air to leave reservoir 300 during priming.

Figure 11:
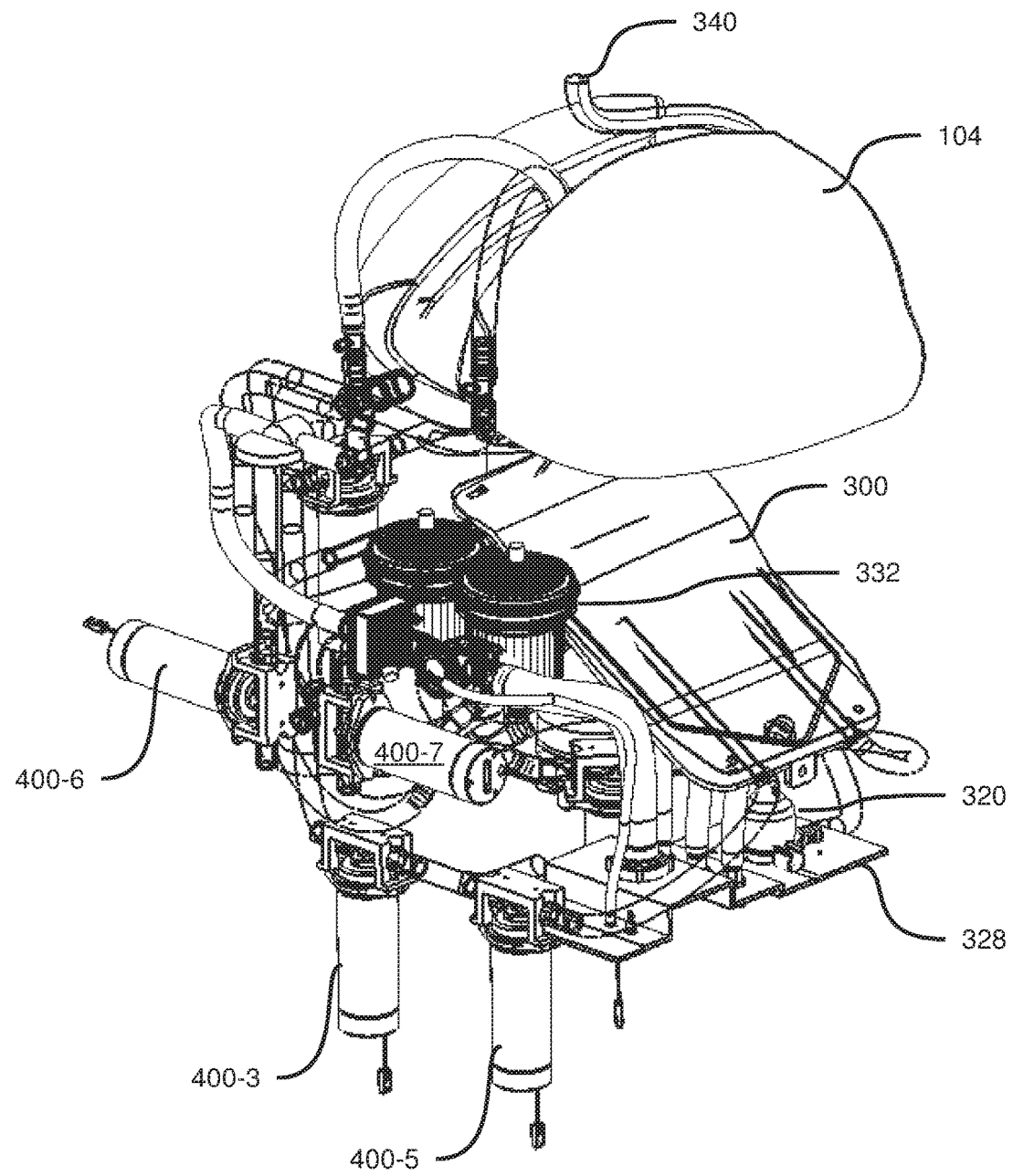
FIG. 11 depicts a partial view of the implementation of FIG. 9, according to a non-limiting embodiment.

Referring to FIG. 11, the arrangement of flow control devices 400-3 and 400-5 (located at surface 200-1 of dock 200), as well as flow control devices 400-6 and 400-7 (located at surface 200-3 of dock 200), is shown. In addition, reservoir 300, pump head 320, leukocyte filters 332 and 334, priming port 340 and mechanical interface 328 are shown. In the present example, interface 328 carries connections for module 324, the ventilation circuit, and pump head 320.

Figure 12:
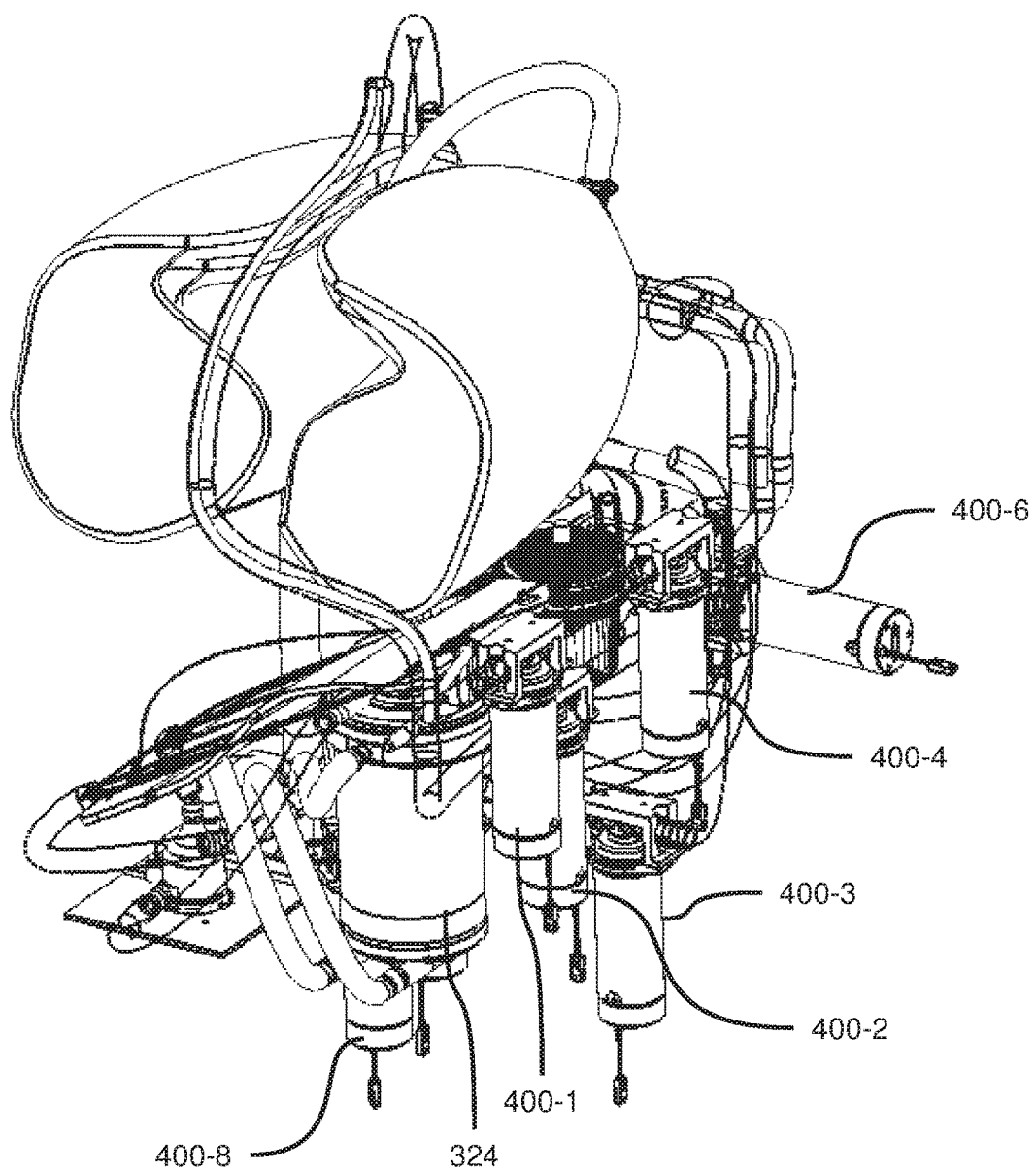
FIG. 12 depicts an additional partial view of the implementation of FIG. 9, according to a non-limiting embodiment.

FIG. 12 depicts another view of the example assembly shown in FIG. 11, in which the remaining flow control devices 400 are depicted. In particular, flow control devices 400-1, 400-2 and 400-4 are shown as protruding from surface 200-2 of dock 200, while flow control device 200-8 is shown as being located at surface 200-1 of dock 200. The position of module 324 is also shown in FIG. 12.

Figure 13:
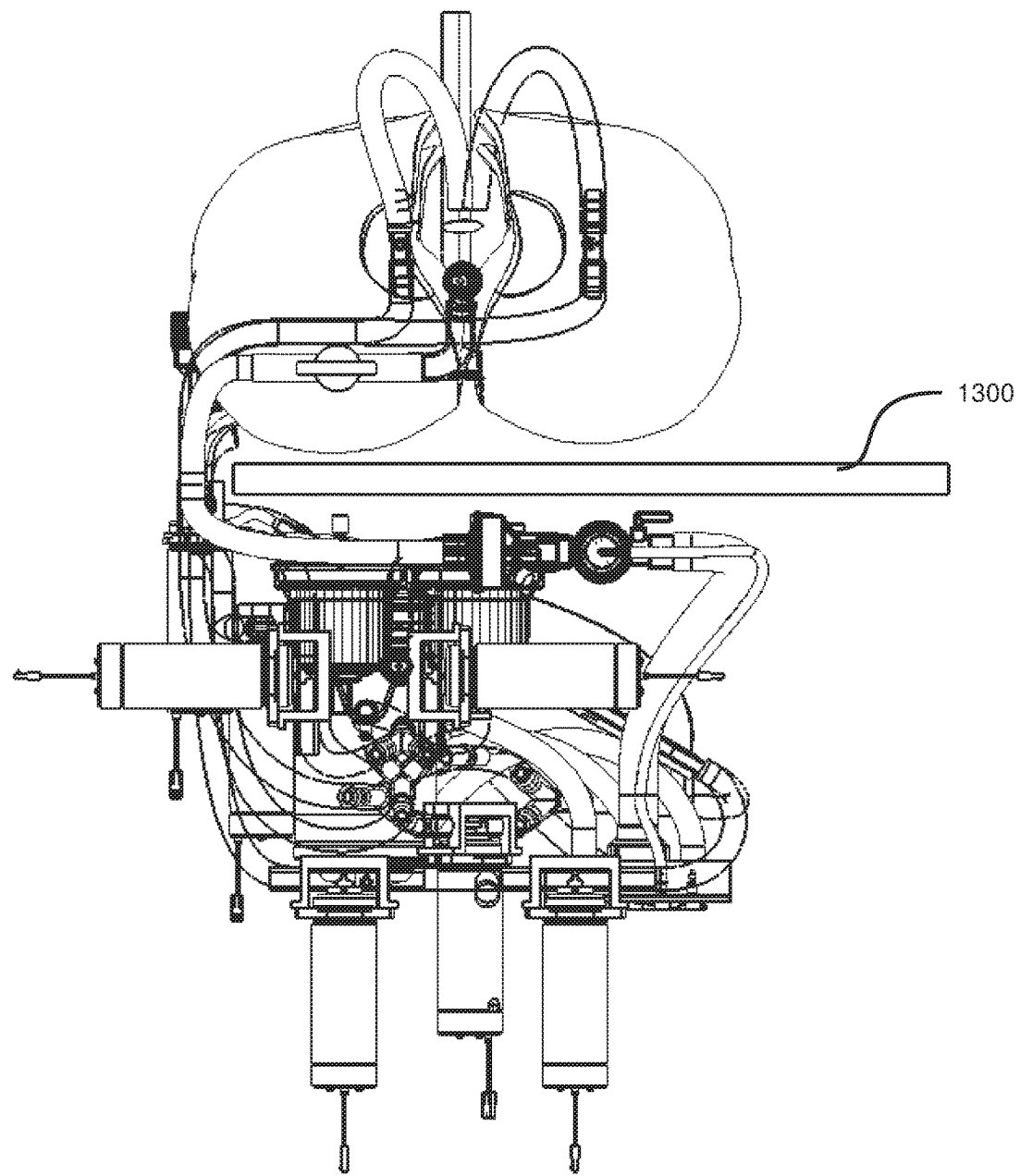
FIG. 13 depicts a further partial view of the implementation of FIG. 9 illustrating an imaging plate, according to a non-limiting embodiment.

Referring now to FIG. 13, it can be seen that fluid conduits 308 are routed from the components of disposable assembly 108 along one side of assembly 108, permitting an imaging plate (e.g. an x-ray plate) to be inserted between organ 104 and those components. As a result, an imaging device located above (in the orientation shown in FIG. 13) organ 104 can be employed to capture images of organ 104 without interference from the internal components of assembly 108.

Figure 14:
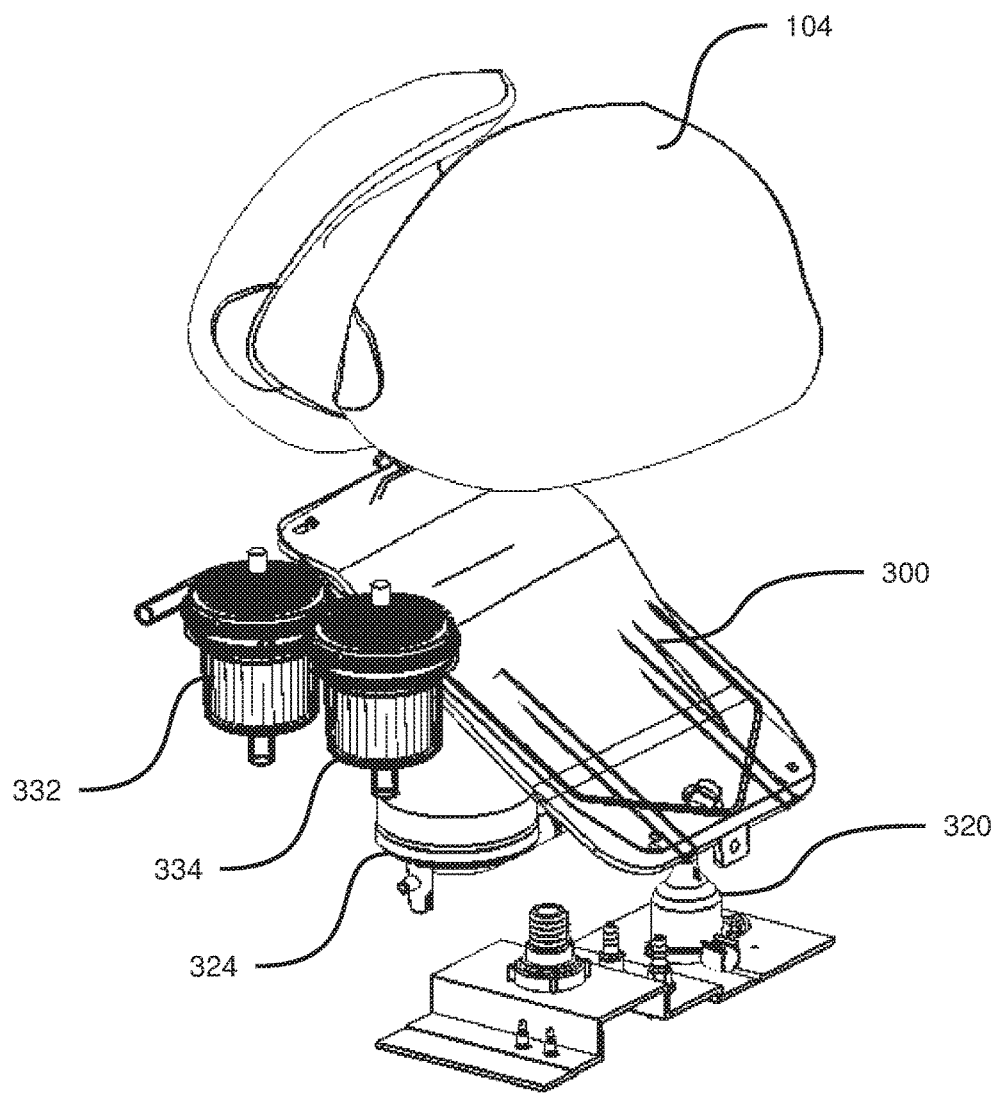
FIG. 14 depicts the relative positions of certain components of the implementation of FIG. 9, according to a non-limiting embodiment.

The components of assembly 108 can also be arranged to increase the effectiveness of the priming of the perfusion circuit (e.g. blocks 705 and 710 of method 700). As shown in FIG. 14, the positioning of reservoir 300, pump head 320, leukocyte filters 332 and 334 and module 324 is such that a hydrostatic gradient is established, beginning at priming port 340 (not shown, but as seen in earlier drawings, located above organ 104), and extending to inlet 1012 of reservoir 300, then to outlet 1004 of reservoir 300 and pump head 320. Although module 324 is positioned physically above pump head 320, the pressure established by priming port 340 is such that module 324 is partially primed via pump head 320. In addition, filters 332 and 334, as well as the remainder of module 324, can be primed by way of the filter priming fluid path mentioned above (i.e. conduits 308-15, 308-12, 308-5, 308-13, 308-4 and 308-3).

In the arrangement illustrated in the accompanying drawings, fluid flow via conduits 308-15, 308-12 and 308-5 to leukocyte filters 332 and 334 during priming may not be sufficient to completely prime filters 332 and 334. In particular, the output ports of filters 332 and 334 (which acts as an input during priming) may be located on the bottom of filters 332 and 334, and priming may therefore not exert sufficient hydrostatic pressure to fully prime filters 332 and 334. In the present embodiment, therefore, filters 332 and 334 are partially primed via conduits 308-15, 308-12 and 308-5. The priming of filters 332 and 334 is completed after pump head 320 has begun operation, to drive perfusion fluid into filters 332 and 334 via conduits 308-3, 308-4 and 308-13. As will now be apparent, in other arrangements, filters 332 and 334 may be placed so as to be fully primed by fluid traveling from port 340 via conduits 308-15, 308-12 and 308-5. In other embodiments, priming of filters 332 and 334 may be achieved via either the filter outlets alone or the filter inlets alone. For example, in some embodiments conduit 308-15 may travel from port 340 to the inlets of filters 334 and 332 (i.e. the tops of the filters as shown in FIG. 14) rather than the outlets of filters 332 and 334 via conduits 308-12 and 308-5, as shown in FIG. 3.

Further, in some embodiments, waste receptacle 304 (not shown) is positioned below outlet 1008 of reservoir 300, such that any fluid in the perfusion circuit may be transferred to waste receptacle gravitationally, in the event of a loss of power or other failure.

The scope of the claims should not be limited by the embodiments set forth in the above examples, but should be given the broadest interpretation consistent with the description as a whole.

The invention claimed is:

1. An organ perfusion device, comprising:
  a disposable assembly including a first housing supporting:
    (i) an inlet for connection to the organ via engagement with an input vessel of the organ, and an outlet for connection to the organ via engagement with an output vessel of the organ; and
    (ii) a perfusion circuit including:
      a reservoir configured to hold a perfusion fluid;
      a waste receptacle;
      a plurality of fluid conduits defining:
        a delivery fluid path connecting the reservoir with the inlet;
        a return fluid path, independent of the delivery fluid path, connecting the reservoir with the outlet; and
        a waste fluid path, independent of the inlet, the outlet and the return fluid path, connecting the reservoir with the waste receptacle for directing the perfusion fluid from the reservoir to the waste receptacle without traversing the organ:
  a reusable assembly including a second housing defining a dock configured to releasably support the disposable assembly in an operational state; the second housing supporting:
    (iii) a first flow control device configured to selectively prevent or allow fluid flow from the reservoir to the organ via the delivery fluid path; and
    (iv) a second flow control device configured to selectively prevent or allow fluid flow from the reservoir to the waste receptacle via the waste fluid path when the first flow control device prevents fluid flow from the reservoir to the organ via the delivery fluid path;
  wherein the first flow control device and the second flow control device are brought into engagement with respective ones of the fluid conduits when the first housing is supported by the dock, to selectively prevent or allow fluid flow via the delivery fluid path and the waste fluid path respectively when the first housing is supported by the dock.

2. The perfusion device of claim 1, the perfusion circuit further comprising:
  a reservoir priming fluid path defined by the plurality of fluid conduits, the reservoir priming fluid path connecting a priming port with the reservoir.

3. The perfusion device of claim 2, the perfusion circuit further comprising:
  an organ priming fluid path defined by the plurality of fluid conduits, the organ priming fluid path connecting the priming port with the organ; and
  a third flow control device configured to selectively prevent or allow fluid flow from the priming port via at least one of the reservoir priming fluid path and the organ priming fluid path.

4. The perfusion device of claim 1, the perfusion circuit further comprising:
  a pump head module on the delivery fluid path, for receiving the perfusion fluid from the reservoir.

5. The perfusion device of claim 4, the perfusion circuit further comprising:
  a conditioning module on the delivery fluid path, for receiving the perfusion fluid from the pump head module.

6. The perfusion device of claim 5, the perfusion circuit further comprising:
  a leukocyte filter on the delivery fluid path, for receiving the perfusion fluid from the conditioning module; the first flow control device disposed between the pump head module and the leukocyte filter.

7. The perfusion device of claim 6, the perfusion circuit further comprising a second leukocyte filter;
  the plurality of fluid conduits further defining an alternate delivery fluid path connecting the reservoir with the inlet via the second leukocyte filter;
  the perfusion device further comprising a third flow control device configured to selectively prevent or allow fluid flow via the alternate delivery fluid path.

8. The perfusion device of claim 1, further comprising:
  an organ support;
  a drain defined in the organ support;
  the plurality of fluid conduits further defining an organ support return fluid path connecting the drain with the reservoir.

9. The perfusion device of claim 8, the plurality of fluid conduits further defining an organ support waste fluid path connecting the drain with the waste receptacle;
  the perfusion device further comprising a third flow control device configured to selectively prevent or allow fluid flow via the organ support waste fluid path.

10. The perfusion device of claim 1, further comprising:
  a controller configured to communicate with each of the flow control devices;
  the controller storing a plurality of operational states each defining a position for each flow control device.

11. The perfusion device of claim 10, further comprising a sensor configured to generate a measurement of a property of the perfusion fluid;
  the controller further configured to receive the measurement and to automatically select one of the operational states based on the measurement, and to control the flow control devices based on the selected operational state.

12. The perfusion device of claim 10, further comprising an input device connected to the controller;
  the controller further configured to receive a selected one of the operational states from the input device, and to control the flow control devices based on the selected operational state.

13. The perfusion device of claim 1, wherein the first and second flow control devices have failure states configured to allow fluid flow from the reservoir to the waste receptacle via the waste fluid path.

14. The perfusion device of claim 1, the plurality of fluid conduits further defining an alternate return fluid path connecting the reservoir with the outlet.

15. The perfusion device of claim 14, further comprising a pressure control valve on the return fluid path.

16. The perfusion device of claim 14, further comprising a third flow control device configured to selectively direct fluid flow via one of the return fluid path and the alternate return fluid path.

17. The perfusion device of claim 1, the dock comprising a wall for supporting the disposable assembly;
   wherein the first and second flow control devices are supported by the reusable assembly to contact the fluid conduits adjacent the wall.

18. The perfusion device of claim 1, the reusable assembly further comprising:
   a controller configured to communicate with each of the flow control devices;
   the controller storing a plurality of operational states each defining a position for each flow control device.

19. The perfusion device of claim 1, the disposable assembly further comprising a gas conduit connected to a gas inlet for connection to the organ; the reusable assembly further comprising a ventilator;
   the disposable assembly and the reusable assembly each comprising mating mechanical interfaces configured to connect the ventilator to the gas conduit.

20. The perfusion device of claim 19, the disposable assembly further comprising a pump head module on the delivery fluid path, for receiving the perfusion fluid from the reservoir;
   the reusable assembly further comprising a pump drive module for driving the pump head module;
   the pump drive module and the pump head module configured to engage via the mating mechanical interfaces.

21. The perfusion device of claim 17, the disposable assembly further comprising a conditioning module in the delivery fluid path; the conditioning module including a heat exchanger and a gas exchanger.

22. The perfusion device of claim 21, the reusable assembly further comprising:
   a heater configured to deliver heated fluid to the heat exchanger; and
   a gas storage device configured to deliver gas to the gas exchanger.

* * * * *